(12) United States Patent
Aman

(10) Patent No.: US 10,625,909 B2
(45) Date of Patent: Apr. 21, 2020

(54) STERILE READY-TO-USE SURGICAL TOOL HAVING WIRELESS CHARGING SYSTEM CAPABILITY

(71) Applicant: Peter M Aman, Austin, TX (US)

(72) Inventor: Peter M Aman, Austin, TX (US)

(73) Assignee: INSURGICAL, INC., Austin, TX (US)

( * ) Notice: Subject to any disclaimer, the term of this patent is extended or adjusted under 35 U.S.C. 154(b) by 838 days.

(21) Appl. No.: 14/710,600

(22) Filed: May 13, 2015

(65) Prior Publication Data

US 2016/0192989 A1 Jul. 7, 2016

Related U.S. Application Data

(60) Provisional application No. 62/099,204, filed on Jan. 2, 2015, provisional application No. 62/009,187, filed on Jun. 7, 2014.

(51) Int. Cl.
*B65D 43/02* (2006.01)
*A61B 17/16* (2006.01)
(Continued)

(52) U.S. Cl.
CPC .......... *B65D 43/02* (2013.01); *A61B 17/1622* (2013.01); *A61B 17/1628* (2013.01); *A61B 50/20* (2016.02); *A61B 50/22* (2016.02); *A61B 50/30* (2016.02); *A61B 50/33* (2016.02); *B65D 77/0406* (2013.01); *G06Q 10/087* (2013.01); *H02J 7/025* (2013.01); *A61B 17/1626* (2013.01); *A61B 2017/00221* (2013.01);
(Continued)

(58) Field of Classification Search
CPC ......... A61B 50/20; A61B 50/22; A61B 50/30; A61B 50/33; A61B 50/31; A61B 2050/3006; A61B 2050/0065; A61B 2050/0086; A61B 2050/3008; A61B 2050/314; A61B 17/1622; A61B 17/1628; A61B 2017/00424; A61B 2017/00734; A61B 19/026; A61C 2202/00; A61C 2204/002; A61C 1/00–0053; A61C 1/02–07; A61C 1/10–12; A61C 1/18–188; A61C 17/00–005; A61C 17/16–40; A61C 3/02–03
USPC ............ 606/79; 173/171, 217, 170; 206/438
See application file for complete search history.

(56) References Cited

U.S. PATENT DOCUMENTS 4,703,852 A * 11/1987 Verdier .................. B25H 3/006
206/349
4,873,461 A 10/1989 Brennan
(Continued)

OTHER PUBLICATIONS

"Inspiration by Orrex," Web page <http://www.orrexmedical.com>, 1 page, Dec. 21, 2014, retrieved from Internet Archive Wayback Machine <https://web.archive.org/web/20141221061519/http://www.orrexmedical.com/> (Year: 2014).*

*Primary Examiner* — David W Bates
*Assistant Examiner* — Marcela I Shirsat
(74) *Attorney, Agent, or Firm* — Clearpat Services, LLC

(57) ABSTRACT

A sterile reusable medical procedure power tool includes an integrated housing having a power and drive housing portion, a handle portion and a battery-housing portion including a battery. The sterile power tool is packaged in a sterile tray or equivalent sterile package including a compartment receiving the sterile power tool. A removable cover is sealingly attached to the sterile package.

4 Claims, 9 Drawing Sheets

(51) Int. Cl.
*A61B 50/30* (2016.01)
*A61B 50/20* (2016.01)
*B65D 77/04* (2006.01)
*A61B 17/00* (2006.01)
*A61B 50/00* (2016.01)
*A61B 50/33* (2016.01)
*G06Q 10/08* (2012.01)
*A61B 50/22* (2016.01)
*H02J 7/02* (2016.01)

(52) U.S. Cl.
CPC ............ *A61B 2017/00424* (2013.01); *A61B 2017/00734* (2013.01); *A61B 2050/0065* (2016.02); *A61B 2050/3008* (2016.02); *A61B 2050/314* (2016.02)

(56) References Cited

U.S. PATENT DOCUMENTS

| | | | | |
|---|---|---|---|---|
| 5,298,821 A * | 3/1994 | Michel | ............ | B25F 5/02 310/47 |
| 5,447,230 A * | 9/1995 | Gerondale | ............ | B65D 5/5002 206/363 |
| 6,059,806 A * | 5/2000 | Hoegerle | ............ | A61B 17/1628 606/180 |
| 6,181,105 B1 * | 1/2001 | Cutolo | ............ | H02J 7/0042 320/115 |
| 6,571,949 B2 * | 6/2003 | Burrus, IV | ............ | B25H 3/02 206/373 |
| 2003/0205029 A1 | 11/2003 | Chapolini | | |
| 2007/0048176 A1 * | 3/2007 | Orrico | ............ | A61L 2/14 422/29 |
| 2007/0290654 A1 | 12/2007 | Govari | | |
| 2009/0292305 A1 | 11/2009 | Kahler | | |
| 2010/0222901 A1 | 9/2010 | Swayze | | |
| 2012/0112690 A1 * | 5/2012 | Stulen | ............ | H02J 7/025 320/108 |
| 2013/0009606 A1 | 1/2013 | Smith | | |
| 2013/0261681 A1 | 10/2013 | Bittenson | | |
| 2014/0052135 A1 | 2/2014 | Aman | | |
| 2014/0251845 A1 | 9/2014 | Roesler | | |
| 2014/0327396 A1 * | 11/2014 | Rejman | ............ | H01M 10/44 320/108 |
| 2015/0196363 A1 | 7/2015 | Aman | | |
| 2016/0211688 A1 * | 7/2016 | Orr | ............ | H02J 7/0044 |

* cited by examiner

STERILE READY-TO-USE SURGICAL TOOL HAVING WIRELESS CHARGING SYSTEM CAPABILITY

CROSS REFERENCE TO RELATED APPLICATIONS

This application is related to and claims priority to U.S. Provisional Application No. 62/009,187, filed Jun. 7, 2014 and to U.S. Provisional Application No. 62/099,204 filed Jan. 2, 2015 which are incorporated herein by reference in their entirety.

BACKGROUND

This disclosure relates to single and limited use surgical power tools and more specifically such tools which can be provided as a pre-packaged, pre-sterilized tool including a pre-installed charged battery.

Important factors for any surgical instrument include sterility, cost of acquisition, maintenance, and reliability during use in the surgical suite. Each of these factors can have a significant impact on the cost of medical care for both the patient and the provider.

In recent years, there has been significant focus on the ever increasing cost of medical care. These cost increases have led to skyrocketing insurance premiums, reduced coverage, reduced reimbursements, increased fees for services, severe reductions in services for some patient groups by some providers, and unfortunately an apparent increase in infections and medical mishaps.

In an effort to reduce costs and improve profitability, both service providers and medical device suppliers are continuously looking for ways to streamline procedures, cut time, cost, and risk from their products and services without reducing the quality of the products or services they provide to their customers. One area to benefit from these savings and improvements has been in the orthopedic surgical field through the use of high precision, battery powered surgical instrumentation. In the late 1960's and early 1970's, battery operated drills were bulky, ill-balanced and required multiple batteries to perform some surgeries due to the limited energy storage capacity and poor efficiency of the electric motors.

Since then, manufacturers have attempted to make batteries more efficient with higher energy storage capacity, reduced size, and improved rechargeable lifespans. Likewise, motor housings such as saw and drill bodies have become more ergonomic, balanced, lightweight and energy efficient. As with many standard hand tools having multiple moving components, instrument manufacturers have reduced weight by utilizing lighter materials such as plastic housings, and gears, and put weight reducing apertures in what were previously solid housings. In some cases, standard mountings for attachments have been replaced with modular fittings, allowing for greater interchangeability and component selections. Additionally, manufacturers have attempted to improve electrical components by upgrading them with more modern components wherever possible.

All of these improvements in equipment construction have improved efficiencies, costs and quality in some areas while at the same time increasing costs for acquisition, maintenance and increasing risks in other ways that were not previously seen or predicted. Often times cost and quality can be inversely proportional to one another. One example of the increased cost and patient risk is seen in the cleaning and maintenance of instruments.

Recent published reports suggest that many of the surgical instruments used in operations were not being cleaned and/or sterilized appropriately in the very hospital facilities that were established and tasked for that purpose. In numerous reports, following cleaning and sterilization, it was noted that upon closer secondary inspection, the inside of small diameter cannulas and intricate mini-components of arthroscopic shavers that are used for many of today's minimally invasive procedures, contained human tissue and bone fragments from previous surgeries. In other cases, modular components of drills and saws such as chucks, drill bits and blades were found to have similar debris or pieces of cleaning brushes and/or bristles embedded in or on them. These investigations have demonstrated that in most cases the instruments were not cleaned according to manufacturer's specifications which has likely lead to many documented cases of serious, multiple, serial infections for subsequent patients. A pilot program conducted by the Centers for Medicare and Medicaid Services (Schaefer et al., 2010; JAMA 2010; 303(22):2273-2279) inspected 1500 outpatient surgery centers and found that 28% had been cited for infectious control deficiencies associated with equipment cleaning and sterilization. The costs to the patients and the hospitals in both expense and liability to deal with these infections can be and has been staggering.

In other cases, critical battery-operated, motorized tools such as drills or bone saws have ceased to function due to dead batteries that no longer maintain their capacity to hold a charge, or due to internal part failure, often attributable to overuse or lack of proper maintenance. The resultant downtime in the operating suite is extremely costly, as the procedure step must be put on hold while replacement or substitute tools are obtained. Wait times may often exceed 20-30 minutes, resulting in additional anesthesia exposure for the patient, additional operating room time (charged to the patient) and potential delays to other procedures where the replacement or substitute equipment had been scheduled for use in a later procedure. Recent estimates (2005) establish the average cost of operating room time to range between $62/min. (range $21.80-$133.12) depending on the procedure. These figures did not include extra resources provided by the hospital for special, non-routine situations which often occur during standard procedures, and did not include the surgeon and anesthesia provider fees, (anesthesia fees are estimated to be $4/min; range $2.20-$6.10).

Hospitals and instrument manufacturers are continuously attempting to find improved ways to reduce risk associated with infection in general, and more recently, specifically from improperly cleaned instruments. One approach has been to use more disposable, single-use instruments such as drills, saw blades and plastic cannulas. Additionally, many laparoscopic devices such as, surgical staplers and trocars, are designed as single use items that are intended to be immediately disposed of after use. Unfortunately, at today's acquisition costs, the total cost of ownership and benefits are not always clear for high-use battery-operated, motorized instruments such as saws, drills and reamers used in orthopedic procedures and the idea of disposable powered instruments has not been readily embraced.

A recent trend in the medical community is reprocessing of single use medical instruments, by parties other than the original equipment manufacturer, instead of discarding them after use. During reprocessing, the medical instruments are disassembled, cleaned and sterilized. They are then reassembled for future use. However, because the medical instruments reprocessed for further use are specifically provided for use during a single procedure, the performance of the medical instruments tends to decline after reprocessing, because the components making up the medical instrument are not adapted for multiple uses and will degrade in performance when used beyond their intended life span. For example, reprocessing of the cutting devices on trocars is intended to extend these devices beyond their intended mission life, but often results in duller cutting edges on the blades because neither the materials used nor the reprocessing method can restore the device to the original manufacturing specifications. A greater force, therefore, is needed to make an initial incision, causing more trauma to the patient. In addition, the use of greater force increases the potential for error during the surgical procedure.

Most hospitals and surgery centers buy high-use, reusable motorized, pneumatic, wired or battery operated, orthopedic surgical equipment and are expected to clean, sterilize, and maintain them internally within the hospital. Unfortunately, the technicians hired to perform this work are typically not qualified or trained to perform this work adequately for the many varieties of powered instruments used. Further, manufacturers rarely provide the hospital/client with the training or diagnostic equipment necessary to evaluate or test the equipment. Often times the hospital employees responsible for cleaning and maintenance are not technicians at all, being paid slightly more than minimum wage, working at a fast pace to merely wash, count, and reload instruments into their appropriate system trays and flash sterilize them as quickly as possible, in an effort to keep the equipment in rotation in the hospital operating rooms, where higher throughput dictates profitability for the hospital or surgery center.

As a result of high throughput requirements, general maintenance is rarely done and preventative monitoring and maintenance is almost never done on this type of equipment. Hospital budgets for internal maintenance of equipment are generally geared toward high-end, multi-million dollar capital equipment such as x-ray and radiological equipment. It is generally assumed that it is faster, simpler, and more economical for the hospital to wait for hand-held instruments, such as drills, saws and reamers to fail, then, send them back to the manufacturer for repair or replacement.

Thus it has become apparent that there is a need for an improved system of cost-effective, battery-operated, motorized tools in conjunction with better cleaning and maintenance protocols which can provide the hospital, surgeon, and most importantly, the patient, with a higher degree of efficiency and cleanliness while reducing risk and keeping the costs of cleaning, maintenance, and repair as low as possible.

SUMMARY

A sterile reusable medical procedure power tool includes an integrated housing having a power and drive housing portion, a handle portion and a battery housing portion including a battery. The sterile power tool is packaged in a sterile tray or equivalent sterile package including a compartment receiving the sterile power tool. A removable cover is sealingly attached to the sterile package.

DETAILED DESCRIPTION

Figure 1:
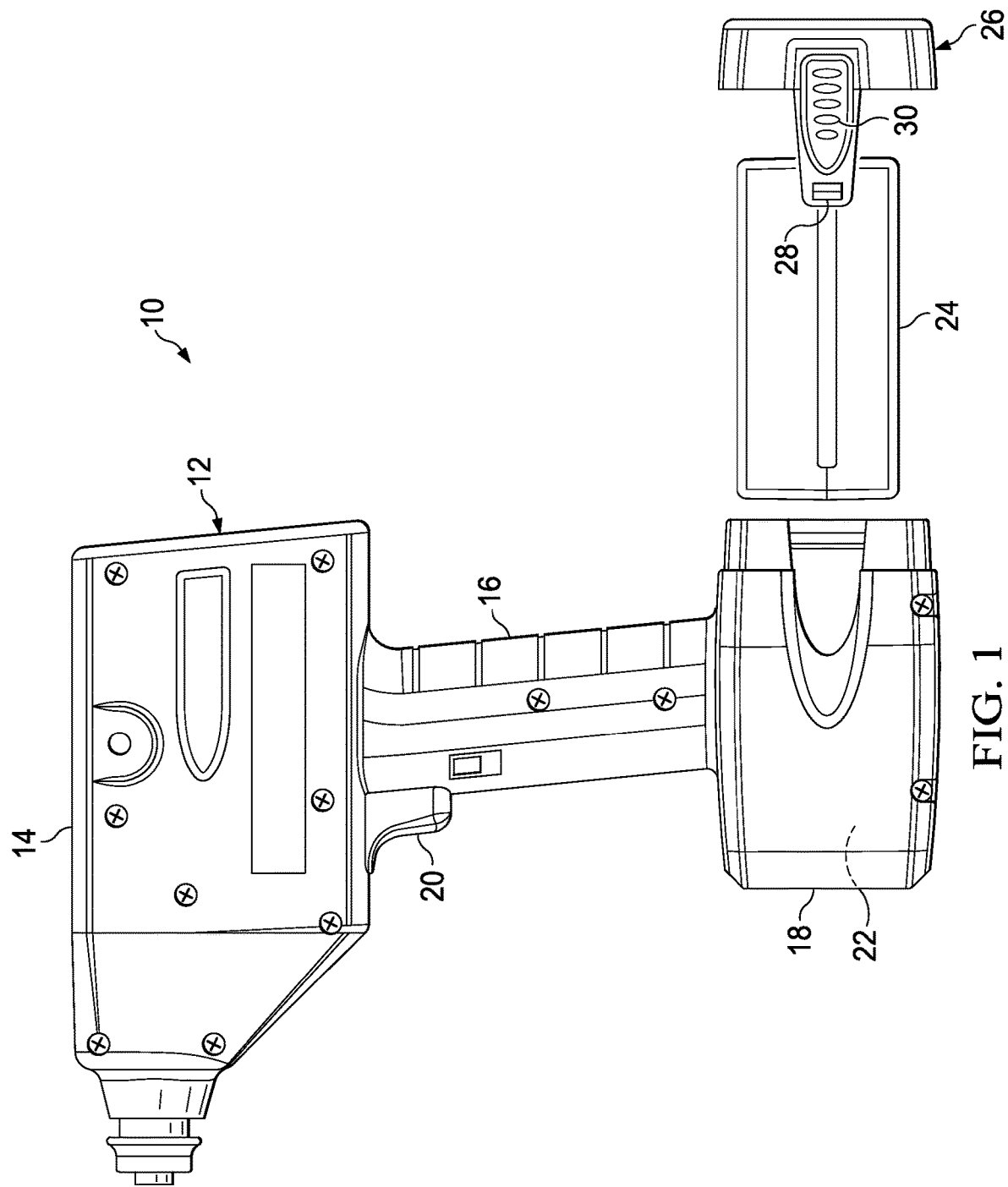
FIG. 1 is a side view illustrating an embodiment of a surgical power tool having an integrated housing including a power and attachment portion, a handle portion, a battery housing portion, a rechargeable battery and a battery housing door.

A medical procedure power tool 10 is illustrated in FIG. 1 and includes an integrated housing 12 having a power and attachment portion 14, a handle portion 16 and a battery housing portion 18. The power and attachment portion 14 contains an electric motor (not shown) and a chuck for securing various tools (not shown) to the tool 10. The handle portion 16 includes a trigger 20, and the battery-housing portion 18 defines a battery compartment 22. The housing 12 is preferably formed of a synthetic material and comprises first and second halves. A battery 24 may be either rechargeable or disposable. A single unit molded door 26 includes a pair of snap-on attachment members 28 and a pair of grip-to-remove members 30. The door 26 is discussed below in more detail.

Figure 2:
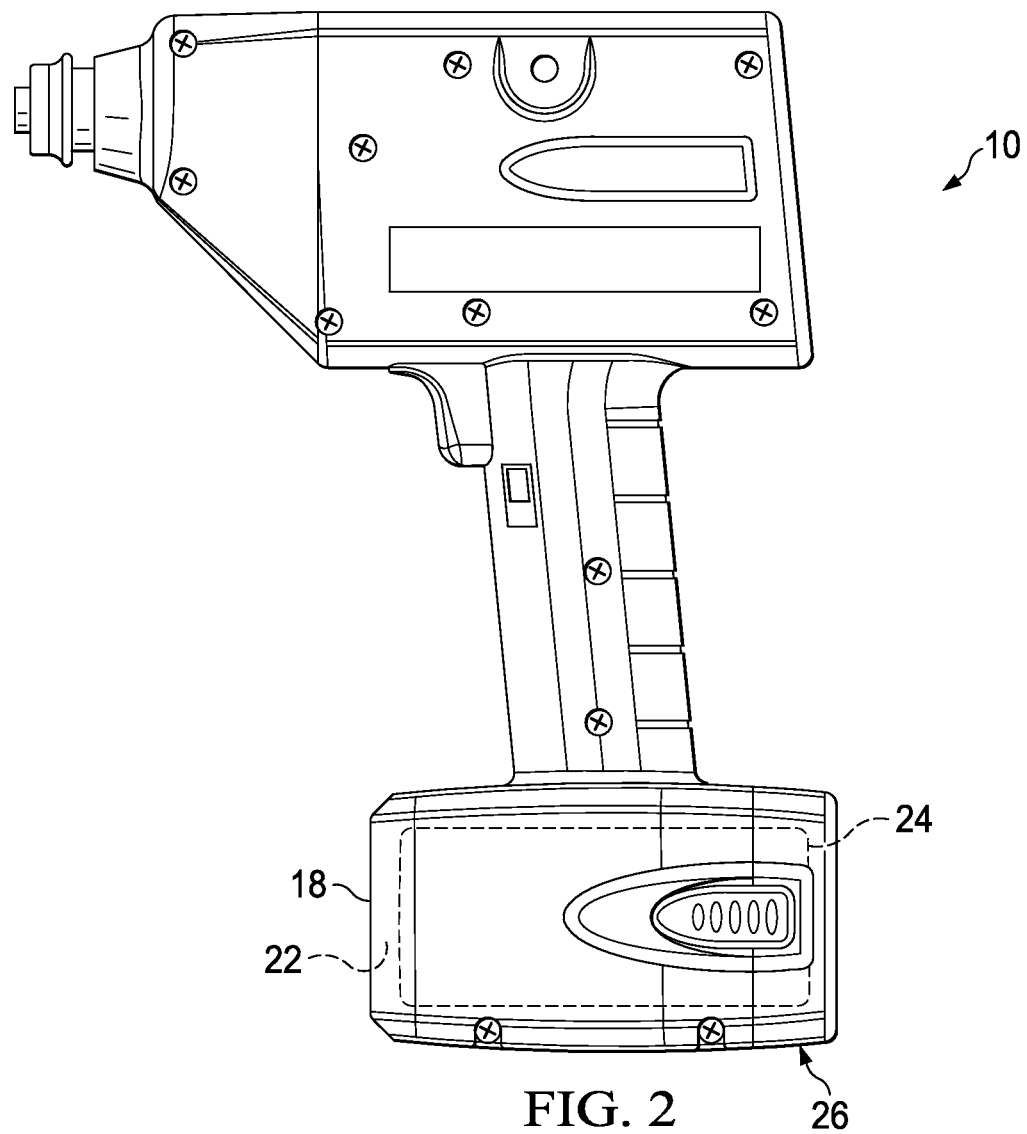
FIG. 2 is a side view illustrating an embodiment of a surgical power tool having the integrated housing of FIG. 1 and a battery in the battery housing portion having the battery housing door attached.
Figure 3:
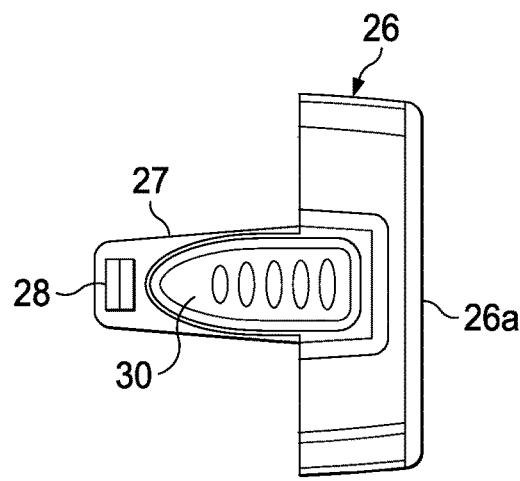
FIG. 3 is a side view illustrating an embodiment of the battery housing door.
Figure 4:
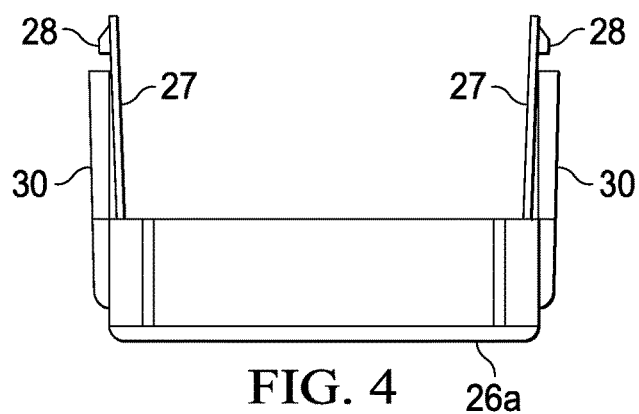
FIG. 4 is a top view of the battery housing door of FIG. 3.
Figure 5:
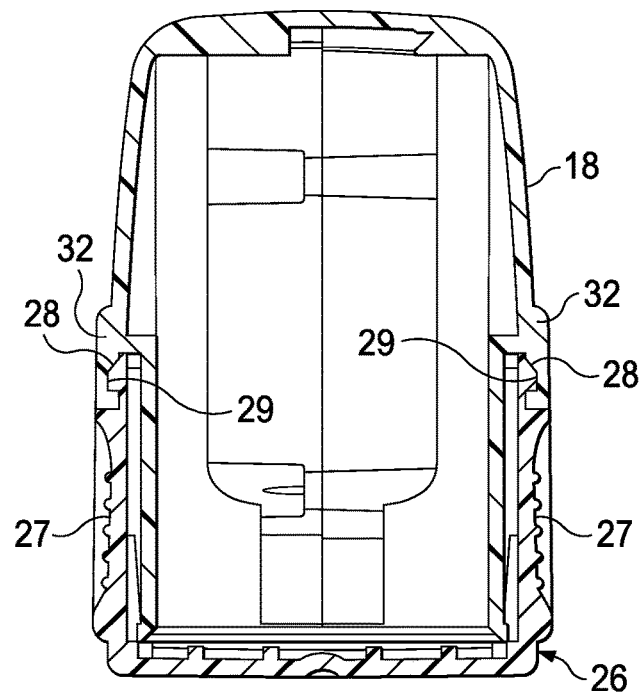
FIG. 5 is a top cut-away view illustrating an embodiment of the battery housing door attached to the battery housing portion.

In FIG. 2, the battery 24 is mounted in the battery compartment 22, and the door 26 is snapped on to the battery housing portion 18. The door 26, FIG. 3, includes an end cap 26a, a pair of ramped snap-on attachment members 28, FIG. 4, and grip-to-remove members 30 which extend on opposed flexible arms 27 from the end cap 26a. The end cap 26a, one of the snap-on attachment members 28 and one of the grip-to-remove members 30 are illustrated in FIG. 3. In FIG. 5, the door 26 is attached to the battery-housing portion 18. As such, the snap-on attachment members 28 are engaged in reliefs 29 in opposed walls 32 of the battery-housing portion 18. For removal of the door 26, a manual pinching action of the opposed flexible arms 27, disengages the attachment members 28 from the respective reliefs 29, and the door 26 is removed from the battery-housing portion 18.

Figure 6:
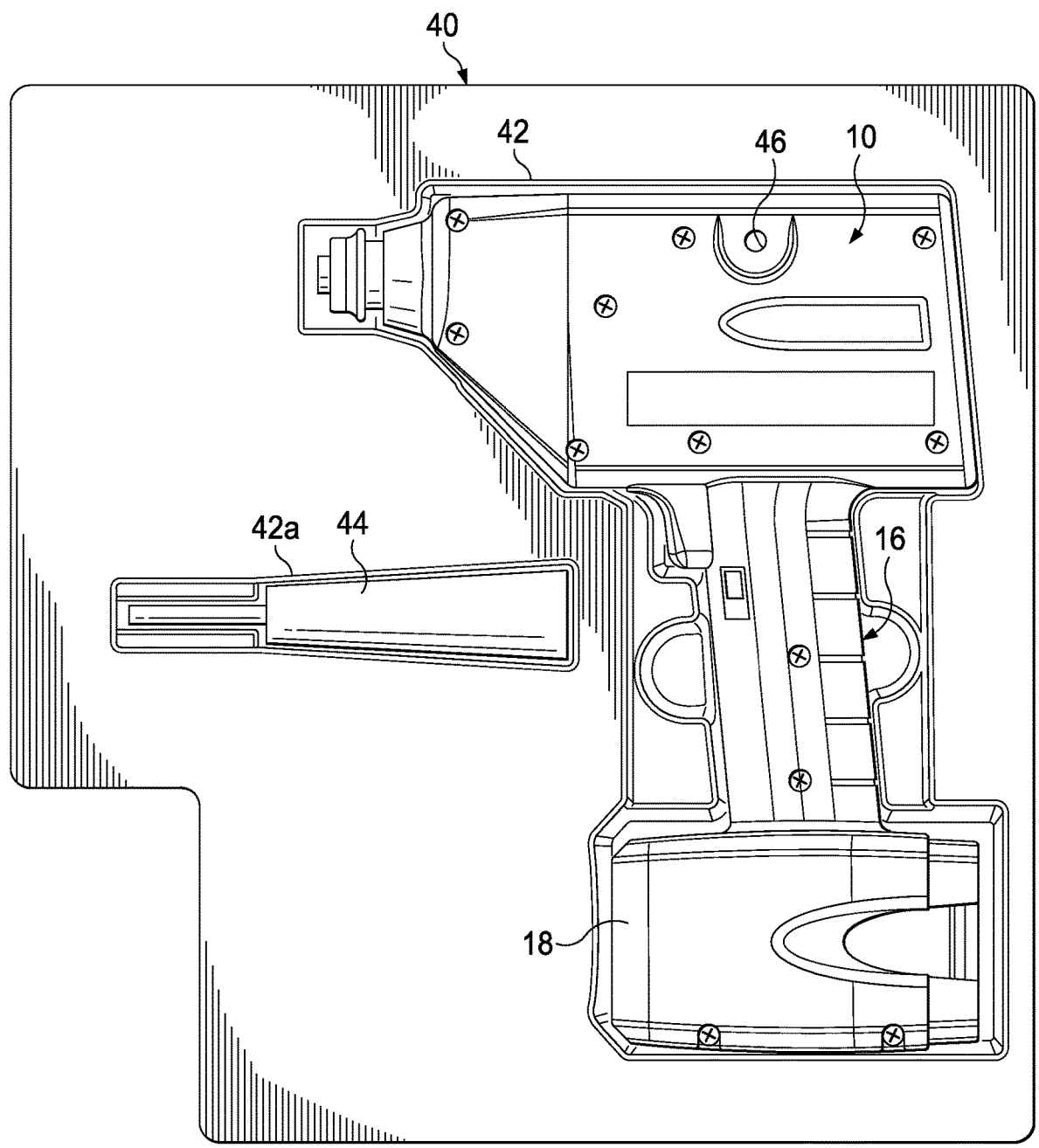
FIG. 6 is a side view illustrating an embodiment of the power tool and an auxiliary part nested in a compartmentalized shipping tray.
Figure 7:
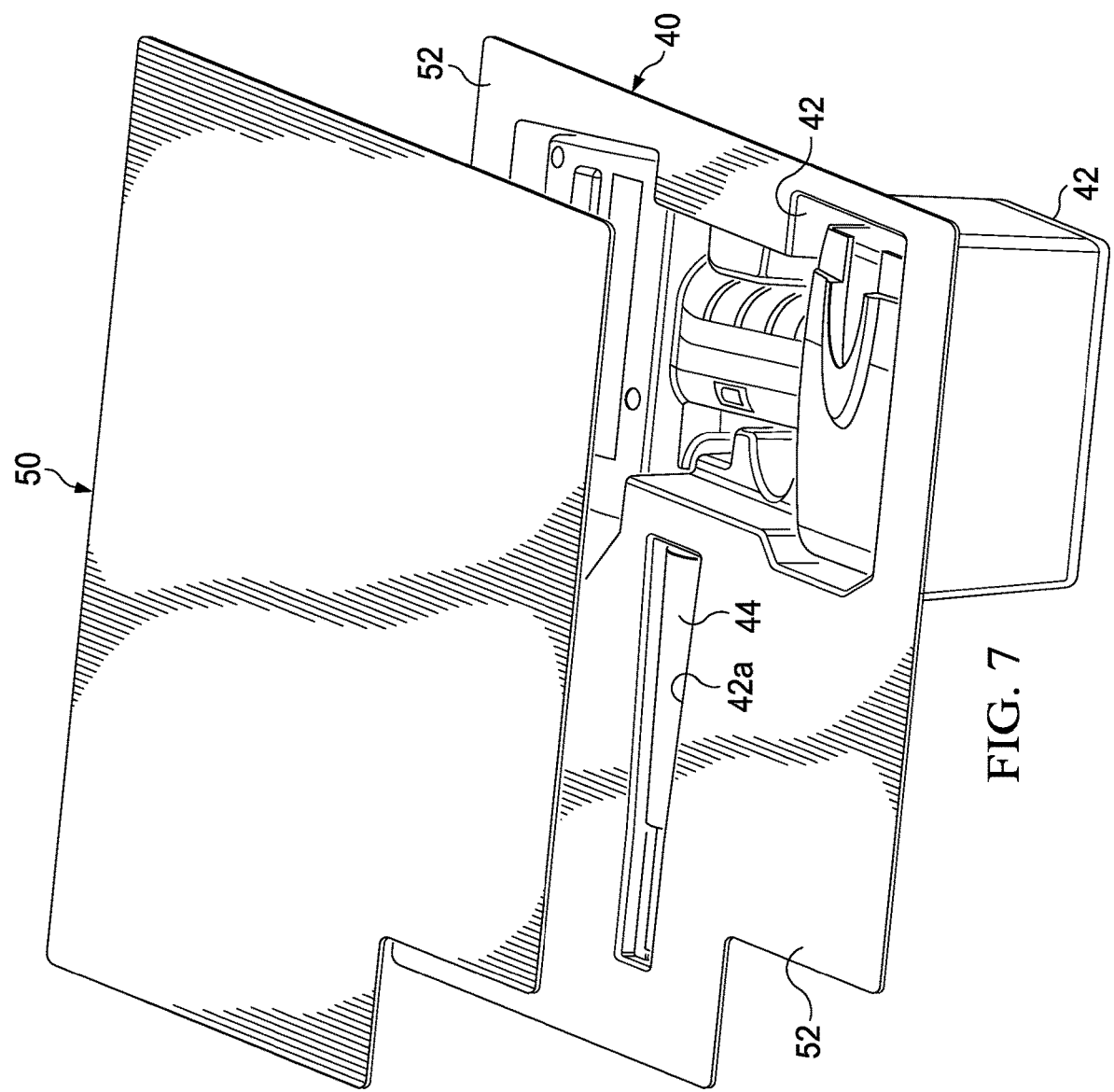
FIG. 7 is a perspective view illustrating an embodiment of a barrier lid for sealing the tray.
Figure 8:
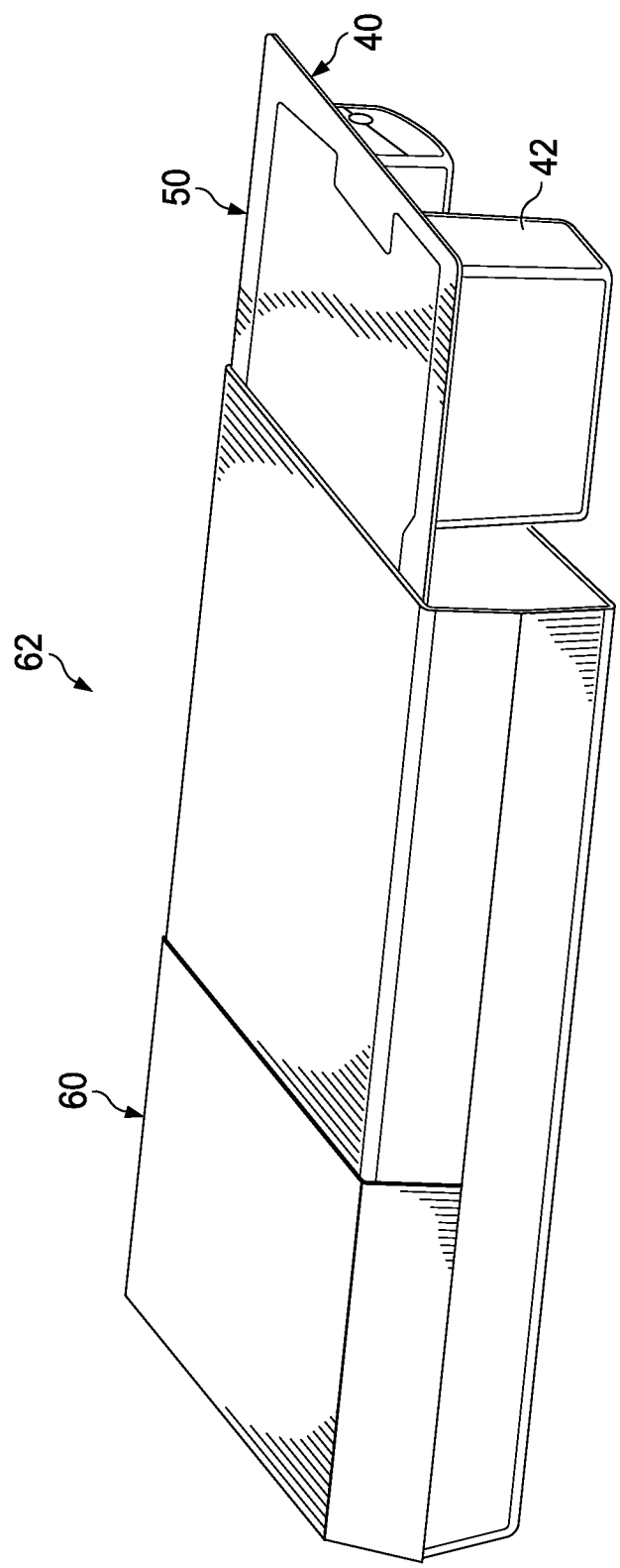
FIG. 8 is a perspective view illustrating an embodiment of the sealed tray and a polyethylene header bag.

A tray 40, FIGS. 6, 7 and 8 includes one or more sunken compartments 42, 42a formed therein. The compartment 42 is formed to receive tool 10, and the compartment 42a is formed to receive an auxiliary handle 44, which if needed, can be attached to tool 10 via a receptacle 46 formed in housing 12. Attachment of handle 44 enhances control of tool 10. Additional compartments may be added to tray 40 as needed to receive other auxiliary parts for use with the tool 10. The compartments 42 and 42a are sufficient to permit nesting of the tool 10 and handle 44 in the tray 40. The tray 40, or any equivalent form of sterile packaging, suitable for shipping tool 10, may be used.

A sealable lid 50, FIG. 7, is attached to a planar surface 52 of tray 40, thus protecting the tool 10 and handle 44, nested in the compartments 42, 42a of tray 40. A header bag 60 receives sealed tray 40, FIG. 8. The bag 60 is sealed and the entire package is shipped ready-for-use in a sterile shipping package 62. The user is required only to remove the sterile tool 10 from the bag 60 and covered tray 40.

With any single-use or limited-use tool system, the cost per tool must be minimized because this cost is spread over a minimum number of procedures. With a traditional tool, the battery enclosure is a separate item from the base tool, requiring an expensive attachment scheme to both secure the battery pack to the tool, and to also connect the electrical terminals to transfer power from the battery into the tool. For a single-use or limited-use tool, it would be preferable to have an integrated battery enclosure to reduce the cost of the combined tool, battery pack, and external battery enclosure.

Additionally, current battery door covers include multiple components, many times a hinge mechanism, that drive up the production costs of a door system. For a single-use or limited-use tool, it would be preferable to have a single component door, with no additional parts required to create a door assembly. This will reduce the total cost per procedure.

The tool and system of this disclosure minimizes cost and complexity for a single- or limited use powered surgical tool, ultimately helping to drive down per-procedure cost. Whereas a traditional powered surgical tool utilizes 3 components (the tool, a battery enclosure, and a battery pack), the new disclosure requires only a tool and a battery pack. This eliminates the need for complicated, expensive hardware required to attach the battery enclosure both physically and electrically to the power tool.

This disclosure is further enhanced by pre-loading the battery which further negates the need for surgical operators to transfer batteries/battery packs to the tool prior to or during surgery.

The disclosure further minimizes cost and complexity for a single- or limited use powered surgical tool, ultimately helping to drive down per-procedure cost. Whereas any existing surgical power tools utilize a complex latching system for the battery door, the current disclosure allows installation, latching, and removal of a battery door system in a single component made of a plastic or other rigid material. This disclosure could be utilized in a format where the door is either installed at the manufacturer's facility, prior to sterilization and eventual use by the medical facility, or it could be installed by medical personnel at the medical facility, after battery installation.

Today's tools, reusable or otherwise, require a hospital to recharge and re-sterilize, as well as transfer a battery into the tool in preparation for the procedure. This system requires the purchase, storage and maintenance of expensive charging systems and batteries. With traditional tools, there was no choice in the matter but to follow this process. With new single-use and limited-use tool systems, tools enter the hospital-prepackaged sterile and ready for use, with the exception of the battery system which is identical to the system utilized with reusable tools. There is a need for a system that eliminates the requirement of the hospital to store, charge and transfer batteries into their tool systems.

Because the standard method of utilizing a powered surgical tool involves both a reusable tool and reusable battery, which in most cases has been purchased by a hospital or some other medical facility, it has also been a standard part of the process to require that these facilities maintain an inventory of batteries and charging systems to power the tools. With single-use and limited-use tools, the tool is now delivered pre-packaged and sterile to the medical facility. As with a traditional reusable tool, there is still a requirement to maintain a stock of batteries and charging systems. This process also requires either the sterilization of the battery pack, and/or the transfer of a battery (sterile or non-sterile) to the tool prior to use.

Figure 9:
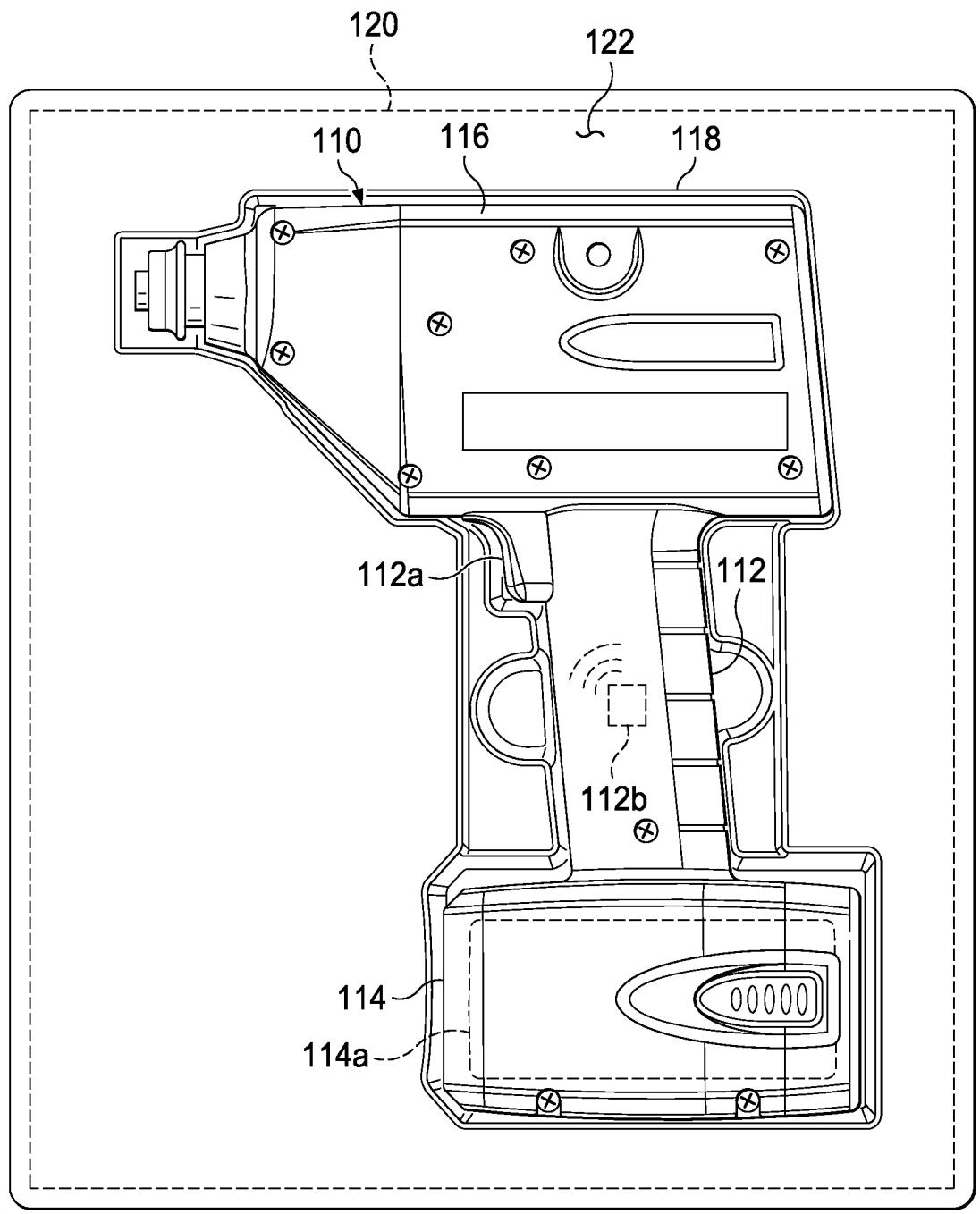
FIG. 9 is a plan view illustrating an embodiment of a sterile packaged re-usable medical procedure power tool.

Alternatively, a power tool 110, FIG. 9, includes a handle portion 112, a power source portion 114 and a tool attachment portion 116. The power source portion 114 includes an integrated, wirelessly charged battery pack 114a. The handle portion 112 includes a trigger portion 112a and an integrated, wireless communication device 112b utilizing Wi-Fi, ultra-wideband, Bluetooth, or any other form of standardized or proprietary communication protocols. The tool 110 illustrates an exemplary power tool for use in medical surgical procedures. The tool 110 is seated in a pocket 118 formed in a tray 120, which is sealed by a cover 122. The tool 110 is sterile packed in tray 120 and is ready for use, including the internal battery pack 114a that is not intended to be field removable. The battery pack 114a includes the capability to be charged wirelessly while remaining sealed in the tray 120. The tray 120, or any equivalent form of sterile packaging, suitable for shipping tool 110, may be used.

Figure 10:
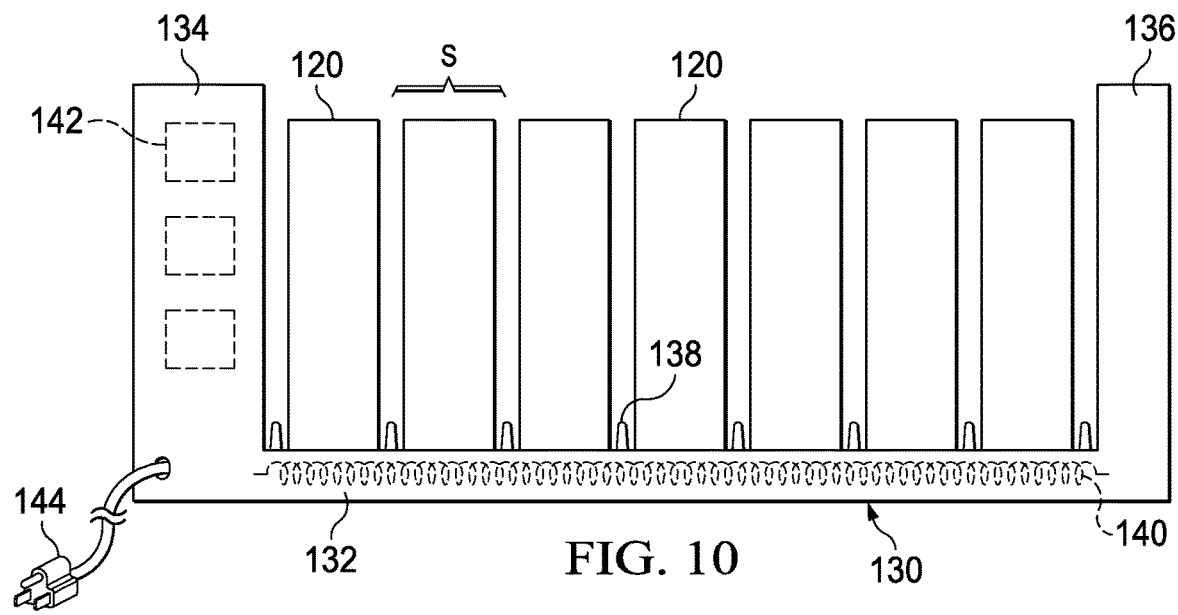
FIG. 10 is a frontal view illustrating an embodiment of a portable tool support member for carrying one or more tools.

An exemplary portable and carryable tool support member 130, FIG. 10, includes a horizontal base member 132 and a pair of vertical end members 134, 136. The base member 132 includes a plurality of slots S, formed by dividers 138 which extend from the base member 132. In this manner, a plurality of the sealed tool-containing trays or other sterile packages 120 can be positioned in the slots S for portability. Base member 132 also includes a charging coil 140 for wireless proximity charging of tools 110 as described above. Energy is selectively provided to charging coil 140 by either of an internal battery source 142 (DC) or by an AC accessible power cord 144.

Figure 11:
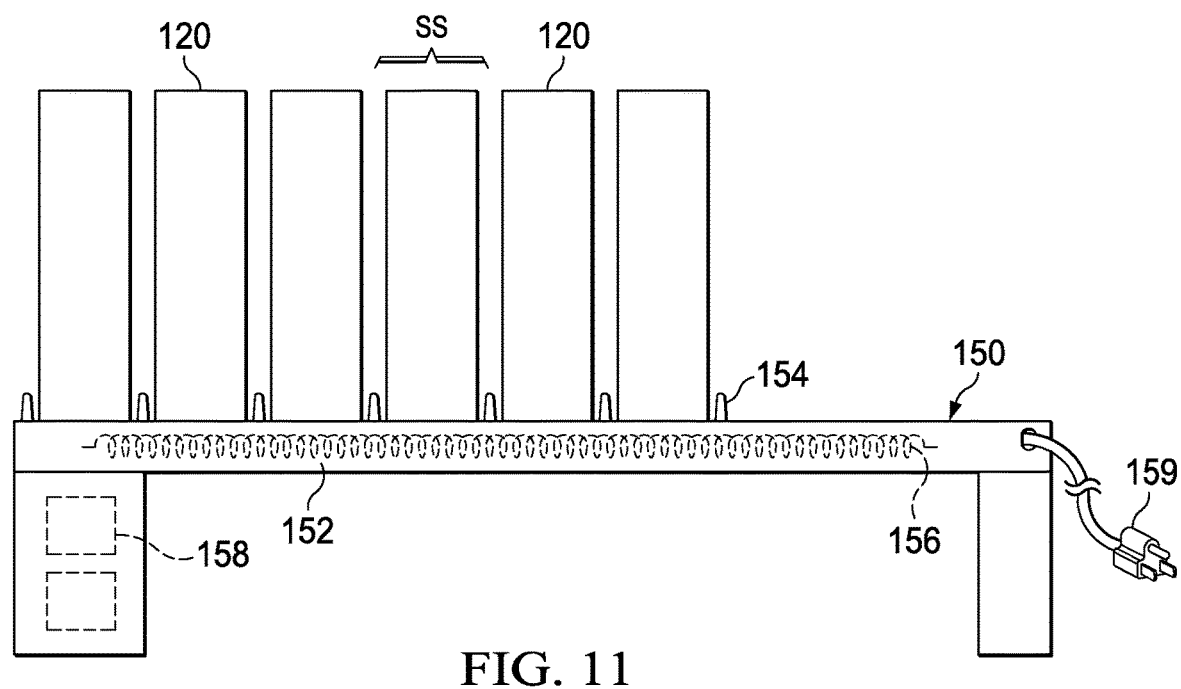
FIG. 11 is a frontal view illustrating an embodiment of a stationary tool support member for storing one or more tools.

A stationary storage shelving unit 150, FIG. 11, similarly includes a base member 152 which also includes a plurality of slots SS, formed by dividers 154 which extend from base member 152. In this manner, a plurality of the sealed, tool-containing trays 120, can be positioned in the slots SS for storage. Base member 152 also includes a charging coil 156 for wireless proximity charging of tools 110 as described above. Energy is selectively provided to charging coil 156 by either of an internal battery source 158 (DC) or an AC accessible power cord 159.

Figure 12:
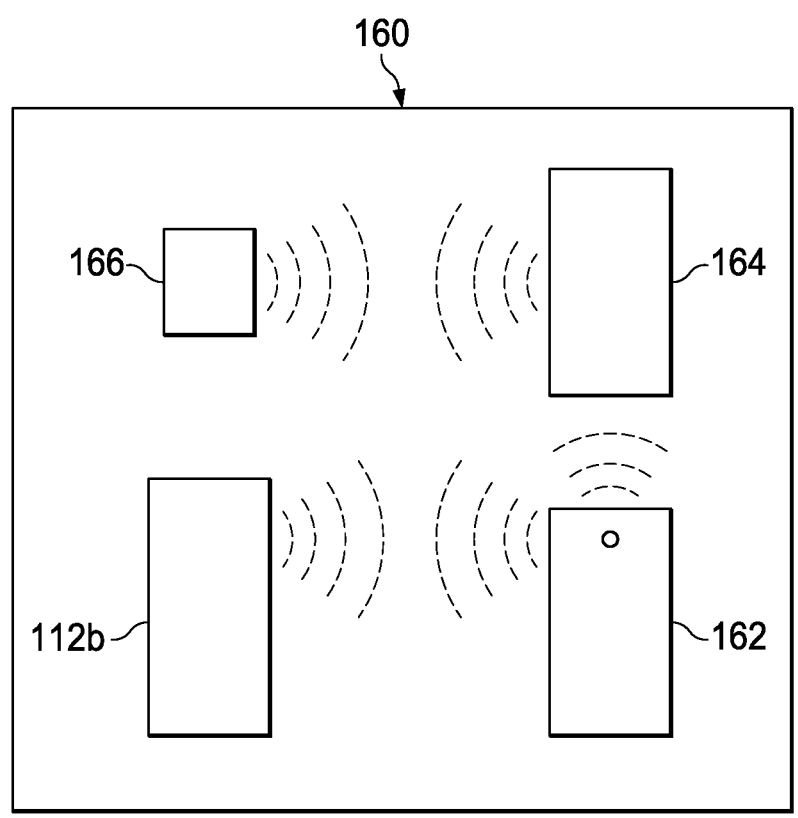
FIG. 12 is a diagrammatic view illustrating an embodiment of a wireless transceiver coupled to communicate with a wireless communication device in the tool, and with a centralized database of a tool supplier, and further illustrates the centralized database being accessible by a user of the tool.

A wireless communication system 160, FIG. 12, includes the wireless communication device 112b, in tool 110, as described above, a wireless transceiver 162, a centralized database 164 of a supplier of tool 110 and a communication device 166 of a user of the tool 110. The transceiver 162 communicates wirelessly with the communication device 112b and centralized database 164 including unique location and other unique data for each tool 110. This allows for enhanced inventory management to regional and hospital-specific product quantities and replenish requirements. In addition, the user communication device 166 can also access some of the data in the centralized database 164 to remain aware of inventory needs.

This new device and system solves the problem of purchasing and managing inventory for batteries and charging systems, thereby reducing costs and complexity for the medical facility using powered surgical tools. A pre-packaged, pre-sterilized tool, including a pre-installed, charged battery, eliminates the need for the operator to own batteries or chargers, and simplifies the process of operating the tool by eliminating the need to transfer a battery to the tool prior to use. Following the procedure, the battery can either be:

- Disposed of with the tool (single-use disposable tool and battery);
- Returned within the tool (limited-use tool with battery); or
- Removed and returned to vendor (single-use disposable tool).

In addition, the power tool may include a wirelessly charged battery pack provided in the tool and an integrated wireless communication device provided in the tool. A wireless transceiver is coupled to communicate with the wireless communication device in the tool, and with a centralized database of a tool supplier, the centralized database may be accessed by a user of the tool.

Although illustrative embodiments have been shown and described, a wide range of modification, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A sterile package deliverable to a medical facility, ready for use, comprising:
   - a sterile medical procedure power tool including an integrated housing having a power and drive housing portion, a handle portion and a battery housing portion including a separable, pre-installed, charged, battery;
   - wherein the pre-installed, charged, battery is disposable, rechargeable or wirelessly rechargeable; and
   - wherein the power tool further comprises a single unit door attachable to the battery housing portion, the door including an attachment member and the battery housing portion further comprises an engagement relief to receive the attachment member; and
   - the sterile power tool being in the sterile package, the package being adhesively sealed by a removable cover and the power tool being immediately ready-to-use upon removal from the sterile package.

2. The sterile package of claim 1, further comprising:
   a sealable header bag for receiving sterile package, which becomes a sterile shipping package for shipping the sterile package.

3. A sterile package deliverable ready-to-use comprising:
   - a sterile medical procedure power tool, the power tool including:
   - an integrated housing including a power and attachment housing portion,
   - a handle portion including a trigger portion,
   - a battery housing portion having a separable, pre-installed, charged, battery disposed therein;
   - wherein the battery housing portion further comprises at least one engagement relief to receive at least one door attachment member, and
   - a single unit door removably attached to the battery housing portion;
   - wherein the single unit removably attached door comprises at least one attachment member extending from the door, and
   - the sterile power tool being in the sterile package, the package being sealed by a removable cover.

4. The sterile package of claim 3, wherein:
   the removable cover comprises a sealable header bag for receiving the sterile package, wherein the removable cover becomes a sterile shipping package for shipping the sterile package.

\* \* \* \* \*